United States Patent [19]

Schwinn et al.

[11] 4,297,344

[45] Oct. 27, 1981

[54] BLOOD COAGULATION FACTORS AND PROCESS FOR THEIR MANUFACTURE

[75] Inventors: Horst Schwinn; Norbert Heimburger, both of Marburg an der Lahn; Gerhardt Kumpe, Wetter; Bernd Herchenhan, Kirchhain, all of Fed. Rep. of Germany

[73] Assignee: Behringwerke Aktiengesellschaft, Marburg an der Lahn, Fed. Rep. of Germany

[21] Appl. No.: 142,962

[22] Filed: Apr. 23, 1980

[30] Foreign Application Priority Data

Apr. 25, 1979 [DE] Fed. Rep. of Germany ....... 2916711

[51] Int. Cl.³ .................... A61K 35/14; A61K 31/00; A61K 37/00
[52] U.S. Cl. .................................... 424/101; 424/176; 424/177; 260/122 B
[58] Field of Search ....................... 424/101, 177, 176; 260/112 B

[56] References Cited

U.S. PATENT DOCUMENTS 3,682,881  8/1972  Fekete et al. ...................... 424/101
3,732,146  5/1973  Heimburger ........................ 435/217

FOREIGN PATENT DOCUMENTS 2057401 of 1972 Fed. Rep. of Germany .
2243688 of 1973 Fed. Rep. of Germany .
51-134878 of 1976 Japan .

OTHER PUBLICATIONS

Soulier et al., Thrombosis Diath. Haemorrh., Suppl. 35, 61-72, (1969).
Merck Index, 9th Ed., (1976) entries 3864, 3869, 7566, 7675.
Chem. Abstr., 77:17050d (1972).
Johnson, Blood, 28, 1011, (1966).
Bohn, Blut 25, 235-248 (1972).
Chem. Abstr., 77:71646r (1972) & 78:120553q (1973).
Schwick et al., "Antithrombin Uterine Hämostase Herz und Blutgerinnung", (1971), pp. 5-16.
Deutsch et al., Science, 170, 1095-1096 (1970).
Wagner et al., Thromb. Diath. Hämor., 11, 64-74 (1964).
Cohn et al., J. Am. Chem. Soc. 68 (1946), 459-475.
Gellis et al., J. Clin. Invest. 27, 239-244 (1948).
Pool et al., New Eng. J. Med., 273 (1965), 1443-1447.

Primary Examiner—Frank Cacciapaglia, Jr.
Attorney, Agent, or Firm—Curtis, Morris & Safford

[57] ABSTRACT

A process for stabilizing the coagulation factors II, VIII, XIII, antithrombin III and plasminogen against heat is described. The preparations obtained according to this process are practically free from coagulable fibrinogen.

4 Claims, No Drawings

BLOOD COAGULATION FACTORS AND PROCESS FOR THEIR MANUFACTURE

The present invention relates to preparations of blood coagulation factors promoting or inhibiting blood coagulation, that is coagulation of fibrinolysis factors. The present invention further relates to a process for the manufacture of such preparations to stabilize them against heat and thus to prevent the transmission of hepatitis when they are administered. The present invention particularly relates to the coagulation factors II, VIII, XIII, to antithrombin III and to plasminogen, the preparation and processes for the stabilization of which are described by way of example. A particular feature of the preparations resides in the fact that they are practically free from coagulable fibrinogen.

Blood coagulation which is induced by various physiological or pathological factors, is a complex process comprising several phases, its course depending on approximately 20 promoting and inhibiting factors. A decrease or an increase in any of these blood coagulation factors may cause disturbances of the blood coagulation, sometimes manifested as diseases.

For example, a liver affection involving a decreased capacity of this organ for synthesis, leads to a drop of the plasma prothrombin (=factor II) level, as a consequence of which spontaneous bleeding, that may be fatal, may take place. In this case prothrombin concentrates are used as instantaneously acting medicaments.

Hemophilia A is caused by a decrease of blood coagulation factor VIII. It is typified by bleeding, especially in the joints and in the musculature. It has been found in recent years that the prognosis of hemophiliacs can considerably be improved by substitution therapy using preparations containing the appropriate factor (factor VIII).

Blood coagulation factor XIII participates in the last phase of blood coagulation by inducing the polymerization of monomeric fibrin. Therefore factor XIII is frequently designated as fibrin-stabilizing factor. A fibrin clot formed in the case of a factor XIII deficiency can be decomposed in relatively easy manner, healing of the wound being disturbed, however. Factor XIII preparations are therefore applied clinically to patients suffering from a congenital or acquired factor XIII deficiency disease.

Antithrombin III has an inhibiting action on thrombin, on the activated factor X(F Xa) and on other serine proteases belonging to the series of the coagulation factors. Thus, it plays an important part in the control of blood coagulation. A relatively small decrease in the antithrombin content in the blood greatly increases thrombohilia.

Plasminogen is a protein that plays a central part in the fibrinolytic activity of the plasma. It represents the zymogen of plasmin, which latter is a protease having a great specificity for fibrin and fibrinogen. Upon completion of a thrombus formation and after the healing of a wound has started, the fibrin clot is decomposed by plasmin by local proteolysis. Plasminogen deficiencies, for example as may occur temporarily during fibrinolysis therapy, may be combated successfully with plasminogen concentrates.

Various processes are known for the manufacture of human factor II, VIII, XIII concentrates, of antithrombin III and of plasminogen concentrates from blood, blood plasma or from placentas.

For example, a factor II preparation may be prepared according to the method of Soulier et al. [Thrombosis Diath. Haemorrh. Suppl. 35, 62 (1969)]. Factor VIII concentrates are obtainable, for example, by the so-called "method IV" [Johnson, A. J.: Blood 28, 1011 (1966)L] using polyethylene glycol.

Factor XIII may be obtained, by way of example, according to the method described by H. Bohn [Blut 25, 235 (1972)] from human placentas. According to Japanese patent Sho 51-134878(1976) of Fukushima, R. et al., factor XIII cncentrates can be heated in the presence of amino acids, monosaccharides or sugar alcohols to 60° C. for 10 hours, however, while suffering from a loss in activity of approximately 50%. During heating each of the three components has a stabilizing effect on factor XIII.

Antithrombin III and plasminogen can be prepared according to processes, for example, as described by H. G. Schwick and N. Heimburger ["Antithrombin, uterine Hämostase, Herz- und Blutgerinnung", Verhandlungen der Deutschen Arbeitsgemeinschaft für Blutgerinnung, 1971, pages 1 to 16, Andersson, L. K. et al., German Auslegeschrift 2,243,688 or D. G. Deutsch and E. T. Mertz, Science 170, 1095 (1970) or Heimburger, N., German Pat. No. 2,057,401].

However, all of the preparations obtained by of the above processes have the disadvantage that the danger of transmitting hepatitis during their use cannot be excluded. In a process for the preparation of albumin [cf. Gellis, S. S. et al.: J. Clin. Invest. 27, 239 (1948)] which is said to guarantee not to transmit hepatitis (this quality being named hepatitis-safe hereinafter), heating is considered a substantial factor. This means that concentrates of the coagulation factors would have to be heated in one method step for a least 10 hours at 60° C. in aqueous solution. The above Japanese patent certainly teaches this treatment of factor XIII. A disadvantage of heating for such a long time is, however, that a considerable loss in yield has to be taken into account. However, processes of the above type for stabilization against heat are, so far, unknown for all of the other preparations. Factor VIII in particular, which is one of the less heatstable coagulation factors, was believed to be unable to withstand heating without suffering from losses in activity or from denaturation. A further problem inherent in known processes, in particular those for preparing factor VIII, consists in separating factor VIII from the accompanying fibrinogen. Both proteins have similar physicochemical properties and cannot be separated from one another quantitatively with methods suitable for large-scale production.

It is known to remove prothrombin, to which the instability of the blood coagulation factors is attributed from plasma fractions with absorbents or precipitation agents. This applies particularly to the fraction that contains factor VIII. It is moreover known to precipitate factor VIII in conjunction with fibrinogen using glycine, to use suitable amino acids, in particular β-alanine, for a partial separation of the fibrinogen from factor VIII and to use mineral absorbents that are capable of binding impurities accompanying the factor VIII preparation under certain circumstances.

However, the problems involved with the instability of the blood coagulation factors against heat and their sensitivity to the action of proteases could not be resolved in a satisfactory manner by any of these known measures or by combining these measures. Even additional precipitation and fractionation steps have not been successful in this respect. It has been ascertained in particular that the β-alanine used as precipitation agent can most probably be made responsible for various incompatibility reactions. Hence, this precipitation agent must not be used in preparations to be used in human therapy.

According to R. H. Wagner et al. [Thromb. Diath. Hämor. 11, 64–74 (1964)] factor VIII can be precipitated with certain specific amino acids. However this reference teaches nothing about the possibility of separating fibrinogen and factor VIII quantitatively by means of a precipitation with amino acids. Even the commercially available factor VIII concentrates with the utmost purity still contain significant quantities of fibrinogen. The same applies to the concentrates prepared according to "method IV [Johnson, A. J.: Blood 28, 1011 (1966)] with the use of polyethylene glycol.

The process described hereinafter is based on the properties and on the findings of factor VIII obtained in accordance with the present invention, on its preparation and stabilization and on experience with concentrates of factors II and XIII, of antithrombin III and of plasminogen.

It has been found, surprisingly, that the disadvantages of the known processes for the preparation of factor VIII can be surmounted by simple modifications of these processes and that it is thus possible to prepare hepatitis-safe factor VIII concentrates free from fibrinogen.

It has been further found, surprisingly, that this modification for factor VIII also results in a increased stabilization of factor XIII, in aqueous solution, as cmpared to the process of Fukushima et al. and that this process is moreover suitable for preparing factor II, antithrombin III and plasminogen.

Finally it has been found that heating in the presence of a specific stabilizer combination gives a preparation that is hepatitis-safe and from which the coagulable fibrinogen can be removed practically quantitatively. Hence the present invention relates to a process for the stabilization of the coagulation factors in aqueous solution against heat and to a method for making a preparation containing coagulation factors which is free from fibrinigen and which is hepatitis-safe.

The subject of the present invention therefore is a process for the stabilization against heat of the coagulation factors II, VIII, XIII, of antithrombin III and of plasminogen, in aqueous solution, which comprises adding to the solution both an amino acid and a monosaccharide, an oligosaccharide or a sugar alcohol.

Stabilization permits heating of the aqueous solution of the coagulation factors sufficiently long that a transmission of causative organisms of hepatitis according to the state of the art is practically excluded. This is particularly valid for processes with additional precipitation, in which the active ingredient remains in the supernatant, while the hepatitis viruses can be removed together with the insoluble precipitate. A preparation that has been kept for approximately 10 hours at a temperature of approximately 60° C. in aqueous solution is considered as being practically hepatitis-safe nowadays.

The present invention in particular relates to a process for obtaining preparations of the coagulation factors II, VIII, XIII, of antithrombin III and of plasminogen, these preparations being practically hepatitis-safe and free from fibrinogen, which comprises adding to a solution containing these factors, preferably a plasma or a placental fraction, from 1.0 to 3.0 mols/l of at least one of the amino acids comprising glycine, α- or β-alanine, hydroxyproline, glutamine, α-, β- or γ-aminobutyric acid, preferably, however, glycine, and from 20 to 60 w/w % of monosaccharides, oligosaccharides or sugar alcohols, preferably from 10 to 30 mols/l of glycine and from 20 to 60 w/w % of saccharose, heating the resulting mixture to a temperature from 30° C. to 100° C., preferably from 60° C. to 100° C. and keeping it for 1 minute to 48 hours, preferably for approximately 10 hours, at this temperature, the shortest period being valid for the highest temperature and vice versa. A maximum yield is obtained only when the pH is adjusted specifically to the individual coagulation factors contained in the solution. Generally a PH from 6.5 to 8.0 is appropriate.

The concentrations of the amino acid or of the carbohydrate in the solution depend on the solubility of these components, concentrations higher than 3.0 mols/l or than 60 w/w %, respectively, being possible provided that the amino acid or the carbohydrate used have a correspondingly higher solubility at the desired temperature. The temperature treatment can alternatively be carried out in several subsequent steps.

With a view to the therapeutic use of the preparations, the solution that contains the coagulation factors can be worked up in the following manner: It is further purified using conventional biochemical processes, optionally protein-stabilizing substances are added thereto, it is filtered under sterile conditions and/or lyophilized. For compounding the measures common for obtaining preparations to be administered parenterally are used.

The preferred combination of glycine and saccharose yields a preparation free from coagulable fibrinogen under the following conditions: 1.0 to 2.5 mols/l of glycine and from 40 to 60 w/w% of saccharose treated subsequently for 15 to 120 minutes at 35° C. to 40° C. and for 5 to 15 minutes at 50° C. to 60° C., at a pH from 6.8 to 7.5.

To prepare a hepatitis-safe preparation, heating for 10 to 20 hours to 60° C. to 70° C. in the presence of saccharose in a concentration from 40 to 60 w/w % and of glycine of from 1.0 to 2.5 mols/l is required. Suitably, fractions in which the factor to be stabilized is enriched according to the cited processes are used. For example, to prepare a factor VIII preparation a fraction obtained according to the so-called method IV (Cohn, J. Amer. Chem. Soc., 68, 459 et seq, (1966) is used. This fraction is precipitated from plasma using 8 v/v % of ethanol under the conditions as specified by Cohn. It contains fibrinogen and factor VIII in addition to various globulins. Moreover, the so-called "cryoprecipitate" which is obtained by a cold precipitation of plasma according to J. G. Pool et al. [New England J. Med. 273, 1443–1447 (1965)] may be used as a starting material. To obtain the cryoprecipitate, fresh plasma is first brought to a temperature of −30° C. and of +4° C. and then the resulting residue is recovered. Each of said precipitates contains more or less prothrombin, which can be readily activated and to which the loss in activity of factor VIII preparations is attributed. It is, therefore, advisable to remove the prothrombin prior to applying the process according to invention, for example by absorption on aluminum hydroxide or on barium sulfate, by precipitation with acridine bases or by chromatography on ion exchanger resins. Aluminum hydroxide in gel suspension is preferably used.

Monitoring the measures used for enriching and purifying factor VIII is familiar from the methods used for determining the respective substances. The process conditions can be directed with these monitoring methods with a view to a satisfactory yield and to a satisfactory purity of the product.

Several processes for determining both fibrinogen and factor VIII have been described in the literature. The fibrinogen is suitably determined according to the following prescription:

1 ml of the fibrinogen-containing solution is placed in the tube of a centrifuge, where it is diluted with 9 ml of physiological salt solution 0.6 ml of a solution containing 60 units of thrombin/ml is added to make the solution coagulate. After standing for 60 minutes at 37° C., the batch is centrifuged in the ultracentrifuge for 30 minutes at approximately 150,000 RCA (relative centrifugal acceleration). The supernatant is decanted and the sediment is washed with three 50 ml portions of physiological salt solution on a suction filter. The sediment is dried overnight in vacuo and the nitrogen content thereof is determined according to Kjeldahl. The protein content in mg, indicated as fibrinogen, is calculated from the data obtained. This method permits both the determination of fibrinogen and of factor VIII.

The factor VIII may be determined, by way of example, according to the following method:

1 part by volume, for example 0.1 ml, of partial thromboplastin, for example prepared according to German Pat. No. 23 16 430, is mixed with one part of plasma deficient in factor VIII and with one part of dilute normal plasma. The temperature of this mixture is kept at 37° C. for 6 minutes. After the addition of one part of a 0.025 molar calcium chloride solution preheated to 37° C., the time taken from the addition of the calcium chloride solution to the formation of a mixture is measured. To make a quantitative determination, the coagulation time of a factor VIII-containing solution is read off on a calibration curve obtained with the aid of a normal plasma dilution series.

1 International Unit (=1 IU) of factor VIII corresponds to the factor VIII activity of 1 ml of normal plasma.

A factor VIII preparation that has been freed of fibrinogen by a precipitation with an amino acid, preferably with glycine in a concentration of from 1 to 3 mols/l, at elevated temperature, can be further purified by various methods, the factor VIII activity being the predominant factor in all of these methods. Particularly suitably, a neutral salt is added to the solution of the factor VIII preparation free of fibrinogen and which contains the amino acids in an amount such that the factor VIII is expelled from the aqueous solution. The factor VIII is suitably precipitated with sodium chloride or with potassium chloride. The salt is suitably added in solid form or in a concentrated solution. The factor VIII precipitates at a final concentration of the salt from 10 to 20 w/v %. The residue can be recovered by centrifugation or by filtration.

To obtain a hepatitis-safe preparation, the residue is heated for at least 10 hours at 60° C. to 70° C. in a solution of from 1 to 3 mols/l of glycine and of from 10 to 60 w/w % of saccharose. Heating may be carried out alternatively using factor VIII preparations that have been prepared by processes different from the described process (Cf. Example 2). The quality of the preparation can frequently be improved if the preparation is centrifuged in a high-speed centrifuge. A product very poor in protein results. Specific activities from 20 to 40 units of factor VIII per mg of protein can be reached. Prior to use in man, the preparation has to be filtered under sterile conditions.

The subject of the present invention is in particular the factor VIII preparation obtainable according to the above process, this preparation being poor in protein, free from coagulable fibrinogen and hepatitis-safe.

The storage-stability of the preparation is suitably improved by the addition of protein-stabilizing substances, for example proteins, amino acids or carbohydrates to the purified factor VIII concentrate. The preparation treated in this manner can, moreover, be lyophilized.

The product according to the invention, when present in a solution suitable for pharmaceutical use, can be used as medicament for the treatment of coagulopathies. It may be administered intravenously, preferably as an infusion, in the therapy and prophylaxis of bleeding caused by factor VIII deficiencies, for example to patients suffering from hemophilia A.

A fraction of human placentas, for example as obtained according to the process of Bohn, H. et al (German Pat. No. 2,063,069), may be used as a starting material for obtaining a factor XIII concentrate. To this end, human deep frozen placentas are extracted with a 0.5% NaCl solution followed by precipitation of the factor XIII from the tissue-free supernatant by means of an acridine base.

After decomposing the acridine adduct with 2.5% NaCl-solution, the factor XIII-containing solution is subsequently purified with cetylpyridinium chloride to liberate it from acid-accompanying protein and from lipids, again treated with the acridine base, decomposed with 2.5% NaCl solution, concentrated by precipitation with ammonium sulfate and further purified by gel filtration. The factor XIII-active fractions are combined and concentrated by pressure filtration or by a second precipitation with neutral salt.

The factor XIII activity is determined with a dilution test [cf. Thromb. diathes. haemorrh. 23, 455 (1970)], which utilizes the different solubilities of the cross-linked fibrin and of the fibrin that has not been cross-linked because of a deficiency of the fibrin-stabilizing factor, in 1% chloroacetic acid. With increasing dilutions of the solution to be determined, fibrin clots are formed by thrombin of fibrinogen free from factor XIII. These clots are incubated with 1% chloracetic acid. That dilution that is still capable of preserving the fibrin clot is determined. It is the factor XIII concentration that is still sufficient for cross-linking. The fibrin clot is dissolved in the next higher dilution.

Normal mixed plasma is used as a reference substance. The factor XIII activity contained in one ml of plasma is defined as one unit. The fibrin-stabilizing activity is calculated from the ratio of the limit values for the dilution of mixed plasma and of test solution.

The hepatitis-safe preparation is prepared by adding glycine and saccharose to the factor XIII concentrate having the above characteristics, followed by heating under conditions as are described for factor VIII. The pH should be kept above 6.8 to ensure a good yield. When run under the above conditions, the process in accordance with the present invention is superior to the process of Fukushima et al., because it results in far higher yields, which can be seen from the following table.

|  | Method according to Fukushima Pat. Sho. 51-134878 | | Method according to the invention | | | |
|---|---|---|---|---|---|---|
| pH-value | 7.0 | 8.0 | 6.3 | 6.3 | 7.0 | 8.0 |
| Stabilizers |  |  |  |  |  |  |
| Saccharose % w/w | — | — | 50 |  | 50 | 50 |
| Glycine mol/l | — | 2.6 | 2 | 2.6 | 2 | 2 |
| Mannitol % w/w | 20 | — | — | 20 | — | — |
| Acitivity prior. to heating U/ml | 133 | 100 | 50 | 42 | 83 | 83 |
| Activity after heating 10 hrs./60° C. U/ml | 0 | 33 | 17 | 5 | 50 | 50 |
| Yield | 0 | 33 | 34 | 12 | 60 | 60 |

The factor XIII concentrate treated in this manner is further purified in the manner described for factor VIII. Ammonium sulfate, when used in a final concentration from 10 to 40 w/v %, has proved appropriate for precipitating the factor XIII.

For use in man, the product is submitted to a filtration under sterile conditions. To stabilize the factor XIII-containing solution for lyophilization, proteins and carbohydrates, preferably in conjunction with human albumin and glucose, are added thereto.

To prepare a hepatitis-safe factor II concentrate, a fraction, obtainable for example according to the process of Soulier, J. P. et al. [cf. Thromb. diath. haemorrh. Suppl. 35, 61 (1969)]. To this end, plasma obtained from blood that has been anticoagulated with EDTA (=ethylenediamino-tetraacetate) is absorbed with tricalcium phosphate and separated by centrifugation to bind the factor II quantitatively to the absorbent. The factor II can be recovered by repeated elutions with portions of 0.2 mol/l of tri-sodium citrate. The combined eluates are further purified by combined precipitations with alcohol and with acetic acid, at a temperature from −8° to +4° C., while the factor II is further concentrated.

The concentrate is taken up in an appropriate buffer, preferably a mixture of sodium chloride and sodium citrate and the activity of the factor II is determined.

The activity is determined by methods generally known to an expert, for example according to the method of Koller, F. et al. [Dtsch. med. Wschr. 81, 516 (1956)]. This comprises mixing one part, for example 0.1 ml, of plasma deficient in factor II and one part of dilute normal plasma, keeping the resulting mixture at +37° C. for 30 seconds, adding 2 parts of calcium-containing thromboplastin, for example prepared according to German Pat. No. 2,356,493, and determining the time interval between addition of thromboplastin and formation of a clot. To make a quantitative determination, the coagulation time of a factor II-containing solution is read off on a calibration curve obtained with the aid of a normal plasma dilution series.

1 Unit of factor II corresponds to the factor II activity of 1 ml of normal plasma.

To kill the hepatitis viruses, glycine and saccharose are added to the factor II solution having the above characteristics and the resulting mixture is heated under conditions as are described for factor VIII.

For further purification, the heated factor II solution is centrifuged, if desired, and the active component is concentrated by precipitation with neutral salt or with alcohol, preferably in an amount from 15 to 40 v/v %, at a pH from 5.0 to 6.5. For use in man, the product is filtered under sterile conditions. An addition of anticoagulants such as heparin may be advisable for stabilization during deep freezing.

An antithrombin III preparation free from infectious virus is obtainable, for example according to the process as described by Andersson, L. K. et al. (German Auslegeschrift No. 2,243,688). To this end, dextran sulfate, heparin or chondroitin sulfate, alone or in the presence of agarose or of lysin-agarose, is rendered insoluble with cyanogen bromide by cross-linking in alkaline medium. After equilibrating of one of these materials in a chromatography column by means of an appropriate buffer, citrated plasma is absorbed thereon. The gel is washed until free of plasma and the antithrombin III-containing fraction is eluted using a buffer of higher molarity. If desired, the preparation is further purified by gel filtration through a molecular sieve. After concentration by precipitation with a neutral salt, preferably ammonium sulfate, the activity of the antithrombin III concentrate is determined.

Both immunological and functional test methods for determining the activity of the antithrombin III concentrate are known to the expert. The method described by Heimburger, N. et al. [Laboratoriumsblätter 28, 65 (1978)] comprises mixing 2 parts, for example 0.2 ml, of antithrombin III reagent with 2 parts of dilute normal plasma, keeping the resulting mixture at +37° C. for 4 minutes, adding 1 part of the mixture to 3 parts of a standardized cattle fibrinogen solution and measuring the time interval between addition and formation of a clot.

To make a quantitative determination, the coagulation time of the antithrombin III-containing solution is read off on a calibration curve obtained with the aid of a normal plasma dilution series. 1 Unit of antithrombin III corresponds to the activity of 1 ml of normal plasma.

To kill the hepatitis viruses, glycine and saccharose are added to the antithrombin III concentrate having the above characteristics in the manner described for factor VIII. After heating, any denaturized protein can be removed by centrifugation. The antithrombin III is concentrated by pressure dialysis or by reprecipitation with a neutral salt, preferably ammonium sulfate used in an amount from 50 to 80 w/v %, and further purified. For use in man, antithrombin III is dialyzed to have a physiological salt concentration, filtered under sterile conditions and optionally lyophilized for prolonged storage.

A hepatitis-safe plasminogen preparation is obtainable, for example according to the process described by Heimburger, N. (German Pat. No. 2,057,401). This process comprises preparing a water-insoluble copolymer into which an aminocarboxylic acid with the amino group in ε-position has been incorporated by polymerization.

Human plasma is brought into contact with this absorbent, whereby the plasminogen is enriched on the absorbent. Thus it is possible to recover plasminogen by elution.

The activity of this fraction can be determined, by way of example, according to the process described by Jacobi, E. et al. [Med. Welt 26, 1996 (1975)]. This test is run in the following manner:

2 Parts, for example 0.2 ml, of plasminogen reagent are mixed with 1 part of dilute normal plasma. The resulting mixture is kept at +37° C. for 3 minutes. 1.5

International Units of thrombin are added and the time interval between addition and formation of a clot is measured. To make a quantitative determination, the coagulation time of the plasminogen-containing solution is read off on a calibration curve obtained with a dilution series of normal plasma. 1 Unit of plasminogen is defined as the fibrinolytic activity contained in 1 ml of normal plasma. It corresponds to 5,000 Christensen units.

Saccharose and glycine are added at a pH from 6.5 to 8.0 to a fraction rich in plasminogen and which has the above characteristics and the mixture is heated under conditions as specified for the factor VIII.

After diluting the solution and after removing any denaturized protein formed by centrifugation, the plasminogen is precipitated with a neutral salt, preferably ammonium sulfate. After dialysis against a isotonic salt solution, it can be filtered under sterile conditions followed by lyophilization.

The present invention will be illustrated in the following examples:

EXAMPLE 1

Hepatitis-safe factor VIII concentrate from human plasma 3.9 Liters of plasma are cooled rapidly to $-30°$ C., left to stand for 24 hours and heated to $+4°$ C. The residue is separated by centrifugation at $+4°$ C. for 15 minutes in a centrifuge at a speed of $2,000\times$ g. The cryoprecipitate obtained in a quantity of 47 g is dissolved in 175 ml of a salt solution of pH 7.0 buffered with sodium citrate, at 25° C. A 2.5% protein solution results. To this protein solution there is added 1/10 volume part of a 25% Al(OH)$_3$—suspension (British Drug House, England) and the resulting mixture is stirred for 20 minutes. The suspension is centrifuged for 30 minutes at $3,000\times$ g. The precipitate is discarded. To the supernatant there is added solid glycine until a final concentration of 2.2 mols/l is reached and the mixture is heated rapidly to 37° C. The mixture is left to stand at this temperature for 30 minutes and cooled subsequently to $+5°$ C. at the same speed. The precipitate formed is separated by centrifugation in 30 minutes at $3,000\times$ g and discarded. The supernatant solution is heated to 56° C., left to stand at this temperature for 5 minutes, and cooled to 20° C. During cooling, the residual fibrinogen precipitates together with globulins. Fibrinogen is separated by centrifugation in 30 minutes at $3,000\times$ g. The supernatant factor VIII solution is brought to a final concentration of 15 w/v % with solid sodium chloride and left to stand at a temperature of 20° C. for approximately 1 hour. During standing, the factor VIII activity precipitates. It is separated by centrifugation in 30 minutes at $3,000\times$ g. The residue is dissolved in 15 ml of a salt solution of pH 7 that has been buffered with sodium citrate.

After centrifugation and clear filtration, 50 w/w % of saccharose and 2 mols/l of glycine are added to the filtrate and the viscous solution is heated to 60° C. for 10 hours. To reduce the viscosity of the heated solution, it is diluted with an equal volume of a buffer of pH 6.8–7 containing 2.2 mols/l of glycine, 0.02 mol/l of citrate and 0.06 mol/l of NaCl. Factor VIII is precipitated from this solution by adding a 35 w/v % salt solution, of pH 6.8 to 7, which contains 2.2 mols/l of glycine and 0.02 mol/l of citrate, until a final concentration thereof of 15 w/v % is reached. The precipitate is separated by centrifugation at $3,000\times$ g and taken up in 12 ml of citrate-NaCl buffer containing 2% of glycine and 0.5% of human albumin. The factor VIII activity of this solution is determined. The solution contains 30 IU/ml, 1 IU corresponding to the activity of 1 ml of fresh citrate mixed plasma of healthy donors.

EXAMPLE 2

Heating of a factor VIII preparation obtained according to the process of Johnson et al. [Blood 28, 1011 (1966)] for inactivating hepatitis viruses 4 Portions of lyophilized factor VIII concentrates each containing approximately 250 IU are taken up at 37° C. in 40 ml of an aqueous solution containing 2.2 mols/l of glycine and 1 g/ml of saccharose. After the contents have completely dissolved, the vial is closed air-tight and incubated in a water-bath at 60° C. for 10 hours.

After cooling to room temperature, the viscous solution is dialyzed 3 times for 3 hours against 50 times its volume of 0.02 mol/l citrate buffer containing 0.06 mol/l of NaCl and 10 mg/ml of glycine.

The protein precipitated during heating, which mainly consists of fibrinogen, is separated by centrifugation and the clear solution is filtered under sterile conditions and lyophilized. The lyophilisate was found to have an activity of approximately 26 IU/ml after dissolution in 20 ml of distilled water. Accordingly, one portion of hepatitis-safe material of approximately 500 IU could be prepared from 4 portions of factor VIII concentrate each containing approximately 250 IU.

EXAMPLE 3

Preparation of a hepatitis-safe factor XIII concentrate from human placentas 15 kg of deep frozen human plancentas, this quantity corresponding to approximately 24 placentas, are micronized and stirred with 15 liters of a 0.5% sodium chloride solution. The resulting mixture is heated to 10° C. and submitted to centrifugation. The fibrin-stabilizing factor is precipitated from the supernatant, free from tissue, at pH 6.0 using a 3% diaminoethoxyacridine lactate solution until a concentration of diaminoethoxyacridine lactate of 8.0%, referred to protein, results, and subsequently isolated by centrifugation.

The centrifuged product is suspended in 9 liters of water at pH 7.0, washed and again centrifuged. The residue ist taken up in 8 liters of a 2.5% sodium chloride solution containing 0.125% of ethylene diaminotetraacetic acid (EDTA) and which had been adjusted to a pH of 7.5, stirred, left to stand for 4 hours and separated from the insoluble matter. Wter is added to the supernatant until a volume of 15 liters is reached. 0.3 Liter of a 3% N-cetyl-pyridinium chloride solution of pH 7.0 is added to the resulting solution to precipitate accompanying proteins and mucopolysaccharides, which latter are separated by centrifugation. 0.75 Liter of a 3% diaminoethoxyacridine lactate solution is added to the supernatant solution, thus precipitating the fibrin-stabilizing factor. The supernatant is siphoned off and the diaminoethoxy acridine lactate precipitate is decomposed with 1 liter of a 5% sodium chloride solution containing 25 g of EDTA at pH 7.5 by stirring for 2 hours. The precipitated diaminoethoxyacridine lactate-chloride is separated by filtration. The fibrin-stabilizing factor is slowly precipitated from the filtrate by adding 25% of solid ammonium sulfate while stirring.

Up to this stage, i.e. precipitation with ammonium sulfate, the placentas have to be worked up as quickly as possible at a temperature between 5° C. and 10° C. to prevent significant losses in activity. After standing for 4 hours, the precipitate is separated by centrifugation.

For further purification, 8 g of the pasty ammonium sulfate are made into a slurry by stirring with 0.01 molar EDTA-solution of pH 7.0, dialyzed against a buffer pH 7,0 consisting of 0.005 mol/l tris(hydroxymethyl)aminomethanehydrochloric acid 0.005 mol/l of EDTA and 0.05% of sodium azide, at a temperature of approximately 4° C.

The pH of the resulting solution is adjusted to 7.0, whereby a precipitate forms, which is separated by centrifugation and discarded. After adjusting the pH to 7.0, the supernatant is purified by column chromatography on cross-linked dextran commercially available as Sephadex ®. A buffer, consisting of 0.005 mol/l tri-HCl, 0.05 mol/l of EDTA and 0.1% of sodium azide (pH 7.0) is used for elution. After passing through the column, the active fractions are collected and the fibrin-stabilizing factor is precipitated therefrom with ammonium sulfate, 25 g of the latter being required per 100 ml of eluate. The precipitate is isolated and dissolved in a 0.005 mol/l tris-EDTA-buffer of pH 7.0.

After a 20 hours' dialysis against a 0.005 mol/l tris-EDTA buffer of pH 7.0, the fibrin-stabilizing factor is precipitated as euglobulin upon adjusting the pH to 5.0. Centrifugation leaves a residue that is dissolved in 2 ml of physiological sodium chloride solution containing 0.01 mol/l of EDTA and which has been adjusted to a pH of 7.8 with 0.2 N sodium hydroxide solution.

2 g of solid saccharose are added to the resulting solution and upon complete dissolution 0.6 g of glycine in solid from is added. The pH of the resulting solution is adjusted to 7.0. The solution is heated to 60° C. for 10 hours and diluted with an equal volume of distilled water. The factor XIII is precipitated by stirring in 0.25 g of ammonium sulfate per 1 ml of solution. The precipitate is recovered by centrifugation and taken up in 2 ml of 0.85% salt solution containing 0.01 mol/l of EDTA.

After adding 0.1 ml of 20% human albumin, the solution is filtered under sterile conditions through a filter impermeable to bacteria, and subsequently dialyzed against a physiological sodium chloride solution and against a physiological sodium chloride solution containing 0.5% of glycose. The fibrin-stabilizing activity of the solution, as compared to that of human plasma, is determined and the solution is diluted with glycose-containing sodium chloride solution until the activity of 4 ml of solution corresponds to the activity of 250 to 300 ml of mixed plasma. Additionally 1 ml of 20% human albumin are added per 25 ml of dilution solution. The product is filtered under sterile conditions, dispensed in vials of 4 ml and lyophilized.

The fibrin-stabilizing activity resulting from 15 kg of placentas gives 12 portions each having 250 ml of plasma activity. Approximately from 40 to 60 liters of blood would be necessary to isolate an equal quantity of fibrin-cross-linking activity from plasma, this quantity of blood corresponding to approximately 80 to 120 blood donations each comprising 500 ml of blood.

EXAMPLE 4

Manufacture of a hepatitis-safe prothrombin concentrate from human EDTA-plasma

400 Blood donations each comprising 500 ml and each of which has been anticoagulated with 50 ml of a solution containing 0.07% of EDTA-sodium and 0.65% of sodium chloride, are used as starting material to obtain approximately 100 liters of plasma, which are further processed in 2 days in the following manner:

800 g of tri-calcium phosphate are added to the plasma at 20° C. and the plasma is stirred for 20 minutes. After separating the absorbent by centrifugation, 5 liters of tri-sodium citrate solution in a concentration of 0.18 mol/l are added to the compact precipitate. After stirring for 30 minutes at 20° C., the solids are separated by centrifugation, the supernatant (eluate 1) is decanted and the residue is stirred for 30 minutes at 20° C. with 2.5 liters of a tri-sodium citrate solution. After a further centrifugation and decantation, the supernatant (eluate 2) is combined with eluate 1 and the residue is discarded.

To separate the finely dispersed absorbent, the combined eluates 1 and 2 are centrifuged for 40 minutes at $2,000 \times$ g. The clear supernatant (7.3 l) is diluted with an equal volume of distilled water and the pH of the dilution is adjusted to 6.8 with 2 N acetic acid. Alcohol is added at $-8°$ C. until a final concentration of 16 v/v % results. The precipitate is separated by centrifugation at 0° to 4° C., the pH of the supernatant is adjusted to 5.2 with 2 N glacial acetic acid and the alcohol concentration is brought to 25 v/v % at $-8°$ C. The precipitate, mainly containing the factor II, is taken up in 1.2 liters of a buffer consisting of 9 parts of a 0.5% sodium chloride solution and of 1 part of 0.1 mol/l of tri-sodium citrate. The pH of the resulting solution is adjusted to 6.8 and subsequently 1 g of saccharose per 1 ml and 0.15 g of glycine per ml are added. The resulting mixture is heated at 60° C. for 10 hours in the closed vessel and diluted with an equal volume of distilled water. Denaturized protein is separated by centrifugation. The pH of the supernatant is adjusted to 5.2 and alcohol is added at $-8°$ C. until a final concentration of 25 v/v % results. The precipitate is submitted to centrifugation and the supernatant is discarded. The precipitate is taken up in 200 ml of the above-described sodium chloride/citrate buffer of pH 6.8, followed by dialysis overnight against a quantity of buffer amounting to 50 times that of the first buffer. After adding 10 USP-units of heparin per ml, the solution is filtered under sterile conditions and lyophilized. 10 Portions each comprising 200 units of factor II are obtained.

EXAMPLE 5

Preparation of a hepatitis-safe antithrombin III concentrate from human plasma

To 5 g of BrCN are added to a solution of 100 cm$^3$ of dextran sulfate (20 mg/cm$^3$). The pH of the solution is adjusted to 11.0 with 5 N NaOH, kept at this level for 30 minutes and lowered to a value of 8.5 with 5 N HCl The mixture is left to stand overnight thereby forming a white, granular gel-like paste. The pasty mass is fed to a small column of 5 mm diameter and of 8 cm length, where it is equilibrated with a buffer of pH 8.5, which contains 0.02 M TRIS, 0.01 M citrate and 0.15 M NaCl.5 cm$^3$ of normal plasma are passed through the column.

Upon passing through the column, the plasma has lost its coagulability. The column is washed with the original buffer and subsequently eluted by increasing the salt concentration stepwise to 1 mol/l NaCl.80 g of ammonium sulfate per 100 ml of solution are added to the eluate and the mixture is stirred for 2 hours. The precipitate formed is separated by centrifugation and taken up in 1 ml of distilled water. 1 g of saccharose and after complete dissolution thereof 0.3 g of glycine are added. The antithrombin-III-containing solution is heated for 10 hours to 60° C.

After adding 4 ml of distilled water and 3 g of ammonium sulfate, the solution is left to stand for 18 hours, the antithrombin III-containing precipitate is submitted to centrifugation and taken up in 1 ml of physiological salt solution. Upon being dialyzed against a physiological salt solution, the preparation contains 1.6 units of antithrombin III per ml, which corresponds to an 80% yield.

EXAMPLE 6

Preparation of a hepatitis-safe plasminogen concentrate from human plasma 100 mg of a copolymer consisting of propylene and maleic acid anhydride, which is specified in greater detail in German Pat. No. 2,057,401, are finely suspended in 0.15 mol/l of a potassium phosphate buffer of pH 7.5 in a total volume of 5 ml. 10 mg of hexamethylene diamine dissolved in 1 ml of the above phosphate buffer are added while stirring. 5 ml of a lysine solution buffered with 2.5% potassium phosphate buffer and having a pH of 7.5 are added through a pipette and the batch is stirred for 24 hours at 4° C. The insoluble cross-linked product is separated by centrifugation, washed lysine-free with physiological salt solution, rinsed with distilled water and lyophilized.

100 mg of the lyophilized cross-linked product are made into a paste with a few ml of human plasma, followed by suspension in 70 ml of human plasma, The pH of the resulting suspension is adjusted to 7.0 with dilute hydrochloric acid and the batch is stirred at 37° C. for 30 minutes. The absorbent is separated by centrifugation and washed with 0.15 M sodium phosphate buffer of pH 6:4 until the wash water is free of proteins. The plasminogen is eluted using 25 ml of a 0.1 mol/l tris-hydroxymethyl-aminomethane solution of pH 10.0, which contains 0.05 mol/l of lysine. The eluate is neutralized with normal hydrochloric acid and subsequently dialyzed against an equal volume of saturated ammonium sulfate solution. The precipitate is separated by centrifugation, taken up in 2 to 3 ml of a 0.1 mol/l disodium biphosphate solution and dialyzed twice against the 100 fold volume of the same solution for 12 hours each time.

1 g of saccharose per ml and 0.15 g of glycine per ml of solution are added to the dialysate and the resulting solution is kept at 60° C. for 10 hours. Thereafter the solution is diluted with an equal volume of distilled water and dialyzed against the twenty-fold its volume of a saturated ammonium sulfate solution. The precipitate is separated by centrifugation, taken up in 3 ml of 0.1 mol/l disodium biphosphate solution and dialyzed against 0.1 mol/l of sodium phosphate buffer of pH 7.5 until an electrolyte equilibrium is reached.

3 ml of a 0.31% plasminogen solution containing 37,300 Christensen units (Chr-U)/ml and 1,200 Chr-U/mg of protein are obtained as the final product. The starting material has a plasminogen titer of 4,000 Chr-U/ml and of 53 Chr-U/mg of protein.

What is claimed is:

1. A method for stabilizing against heat an aqueous solution containing at least one member selected from the group consisting of coagulation factors II, VIII, XIII, antithrombin III, and plasminogen, which method comprises adding to said solution from 1.0 to 3.0 mols per liter of at least one amino acid selected from the group consisting of glycine, α- and β-alanine, hydroxyproline, glutamine, and α-, β-, and γ-aminobutyric acid and from 20 to 60 w/w percent of a carbohydrate selected from the group consisting of monosaccharides, oligosaccharides, and sugar alcohols.

2. A method as in claim 1 wherein said amino acid is glycine and said carbohydrate is saccharose.

3. A method for making a hepatitis-safe preparation of at least one member selected from the group consisting of coagulation factors II, VIII, XIII, antithrombin III, and plasminogen, which method comprises first stabilizing against heat an aqueous solution containing at least one of said members by adding to said solution from 1.0 to 3.0 mols per liter of at least one amino acid selected from the group consisting of glycine, α- and β-alanine, hydroxyproline, glutamine, and α-, β-, and γ-aminobutyric acid and from 20 to 60 w/w percent of a carbohydrate selected from the group consisting of monosaccharides, oligosaccharides, and sugar alcohols, then heating the resulting heat-stabilized aqueous solution at a temperature from 30° C. to 100° C. for a period of time from one minute to 48 hours at a pH from 6.5 to 8.0, whereby hepatitis virus present in said solution is inactivated, and then recovering at least one member from said solution.

4. A method as in claim 3 wherein said amino acid is glycine, said carbohydrate is saccharose, and said heat-stabilized solution is heated at a temperature from 60° C. to 100° C. for approximately 10 hours.

* * * * *